United States Patent
Kassem

(10) Patent No.: US 8,870,768 B2
(45) Date of Patent: Oct. 28, 2014

(54) WIRELESS FLOW SENSOR METHODS

(71) Applicant: DePuy Synthes Products, LLC, Raynham, MA (US)

(72) Inventor: Salim Kassem, North Attleboro, MA (US)

(73) Assignee: DePuy Synthes Products, LLC, Raynham, MA (US)

( * ) Notice: Subject to any disclaimer, the term of this patent is extended or adjusted under 35 U.S.C. 154(b) by 0 days.

(21) Appl. No.: 13/875,536

(22) Filed: May 2, 2013

(65) Prior Publication Data

US 2013/0245404 A1 Sep. 19, 2013

Related U.S. Application Data

(62) Division of application No. 11/931,127, filed on Oct. 31, 2007, now Pat. No. 8,454,524.

(51) Int. Cl.
*A61B 5/07* (2006.01)
*A61B 5/00* (2006.01)
*A61M 27/00* (2006.01)

(52) U.S. Cl.
CPC .............. *A61B 5/0015* (2013.01); *A61B 5/075* (2013.01); *A61M 2205/3331* (2013.01); *A61M 2205/3523* (2013.01); *A61B 5/0031* (2013.01); *A61M 27/006* (2013.01)
USPC ................... 600/302; 600/561; 604/8; 604/9

(58) Field of Classification Search
CPC .... A61B 5/031; A61B 5/0031; A61B 5/0002; A61M 27/006; A61M 2205/3331; A61M 2205/3523
USPC ......... 600/301, 486, 488, 504, 561, 309, 465, 600/468, 505; 604/9, 8
See application file for complete search history.

(56) References Cited

U.S. PATENT DOCUMENTS 2,396,351 A 3/1946 Thompson
3,886,948 A 6/1975 Hakim
(Continued)

FOREIGN PATENT DOCUMENTS

AU 729467 2/2001
CN 2555770 Y 6/2003
(Continued)

OTHER PUBLICATIONS

[No Author Listed] Surface Micromachined Pressure Sensor Technologies, product data sheet of Institut Mikroelektronische Schaultungen und Systeme, pp. 1-2, Sep. 2002.

(Continued)

*Primary Examiner* — Jacqueline Cheng
*Assistant Examiner* — Puya Agahi
(74) *Attorney, Agent, or Firm* — Mintz Levin Cohn Ferris Glovsky and Popeo, P.C.

(57) ABSTRACT

Devices and methods useful for non-invasively measuring and indicating a rate of fluid flow are disclosed. In one embodiment, a sensor housing adapted to received fluid flow therethrough is provided. A radio frequency tag and a masking element can be disposed in the sensor housing. The masking element and the radio frequency tag can be configured to move relative to one another. The relative positions or movement can alter the response of the radio frequency tag to a wireless signal (which can be emitted from an external reading device, for example) and thereby indicate a rate of fluid flowing through the housing. For example, in some embodiments, the masking element can selectively cover at least part of the radio frequency tag in correspondence to the flow rate, which can change a characteristic of the radio frequency tag's response to the wireless signal.

3 Claims, 12 Drawing Sheets

(56) References Cited

U.S. PATENT DOCUMENTS

| | | |
|---|---|---|
| 3,960,142 A | 6/1976 | Elliott et al. |
| 3,976,278 A | 8/1976 | Dye et al. |
| 4,077,882 A | 3/1978 | Gangemi |
| 4,114,603 A | 9/1978 | Wilkinson |
| 4,127,110 A | 11/1978 | Bullara |
| 4,135,509 A | 1/1979 | Shannon |
| 4,237,900 A | 12/1980 | Schulman et al. |
| 4,332,255 A | 6/1982 | Hakim et al. |
| 4,385,636 A | 5/1983 | Cosman |
| 4,387,715 A | 6/1983 | Hakim et al. |
| 4,421,124 A | 12/1983 | Marshall |
| 4,494,950 A | 1/1985 | Fischell |
| 4,540,400 A | 9/1985 | Hooven |
| 4,551,128 A | 11/1985 | Hakim et al. |
| 4,556,086 A | 12/1985 | Raines |
| 4,576,181 A | 3/1986 | Wallace et al. |
| 4,593,703 A | 6/1986 | Cosman |
| 4,595,390 A | 6/1986 | Hakim et al. |
| 4,611,578 A | 9/1986 | Heimes |
| 4,615,691 A | 10/1986 | Hakim et al. |
| 4,625,730 A | 12/1986 | Fountain et al. |
| 4,660,568 A | 4/1987 | Cosman |
| 4,676,772 A | 6/1987 | Hooven |
| 4,711,249 A | 12/1987 | Brooks |
| 4,718,425 A | 1/1988 | Tanaka et al. |
| 4,723,556 A | 2/1988 | Sussman |
| 4,727,887 A | 3/1988 | Haber |
| 4,772,257 A | 9/1988 | Hakim et al. |
| 4,785,822 A | 11/1988 | Wallace |
| 4,787,886 A | 11/1988 | Cosman |
| 4,820,265 A | 4/1989 | DeSatnick et al. |
| 4,841,977 A | 6/1989 | Griffith et al. |
| 4,850,358 A | 7/1989 | Millar |
| 4,885,002 A | 12/1989 | Watanabe et al. |
| 4,893,630 A | 1/1990 | Bray, Jr. |
| 5,004,472 A | 4/1991 | Wallace |
| 5,009,662 A | 4/1991 | Wallace et al. |
| 5,021,046 A | 6/1991 | Wallace |
| 5,163,904 A | 11/1992 | Lampropoulos et al. |
| 5,201,753 A | 4/1993 | Lampropoulos et al. |
| 5,252,962 A | 10/1993 | Urbas et al. |
| 5,265,606 A | 11/1993 | Kujawski |
| 5,280,789 A | 1/1994 | Potts |
| 5,321,989 A | 6/1994 | Zimmer et al. |
| 5,337,612 A | 8/1994 | Evans |
| 5,385,514 A | 1/1995 | Dawe |
| 5,396,899 A | 3/1995 | Strittmatter |
| 5,417,235 A | 5/1995 | Wise et al. |
| 5,425,713 A | 6/1995 | Taylor et al. |
| 5,431,057 A | 7/1995 | Zimmer et al. |
| 5,431,629 A | 7/1995 | Lampropoulos et al. |
| 5,437,627 A | 8/1995 | Lecuyer |
| 5,449,345 A | 9/1995 | Taylor et al. |
| 5,490,514 A | 2/1996 | Rosenberg |
| 5,591,171 A | 1/1997 | Brown |
| 5,622,869 A | 4/1997 | Lewis et al. |
| 5,630,836 A | 5/1997 | Prem et al. |
| 5,643,194 A | 7/1997 | Negre |
| 5,651,767 A | 7/1997 | Schulman et al. |
| 5,704,352 A | 1/1998 | Tremblay et al. |
| 5,711,302 A | 1/1998 | Lampropoulos et al. |
| 5,716,342 A | 2/1998 | Dumbraveanu et al. |
| 5,721,382 A | 2/1998 | Kriesel et al. |
| 5,797,403 A | 8/1998 | DiLorenzo |
| 5,803,917 A | 9/1998 | Butterfield et al. |
| 5,836,886 A | 11/1998 | Itoigawa et al. |
| 5,873,840 A | 2/1999 | Neff |
| 5,928,182 A | 7/1999 | Kraus et al. |
| 5,935,083 A | 8/1999 | Williams |
| 5,970,801 A | 10/1999 | Ciobanu et al. |
| 5,993,395 A | 11/1999 | Shulze |
| 5,993,398 A | 11/1999 | Alperin |
| 6,010,482 A | 1/2000 | Kriesel et al. |
| 6,025,725 A | 2/2000 | Gershenfeld et al. |
| 6,071,267 A | 6/2000 | Zamierowski |
| 6,083,174 A | 7/2000 | Brehmeier-Flick et al. |
| 6,111,520 A | 8/2000 | Allen et al. |
| 6,113,553 A | 9/2000 | Chubbuck |
| 6,120,457 A | 9/2000 | Coombes et al. |
| 6,158,965 A | 12/2000 | Butterfield et al. |
| 6,171,252 B1 | 1/2001 | Roberts |
| 6,208,254 B1 | 3/2001 | McQueen et al. |
| 6,248,080 B1 | 6/2001 | Miesel et al. |
| 6,264,612 B1 | 7/2001 | McConnell et al. |
| 6,278,379 B1 | 8/2001 | Allen et al. |
| 6,316,522 B1 | 11/2001 | Loomis et al. |
| 6,371,976 B1 | 4/2002 | Vrzalik et al. |
| 6,416,291 B1 | 7/2002 | Butterfield et al. |
| 6,439,538 B1 | 8/2002 | Ito |
| 6,447,449 B1 | 9/2002 | Fleischman et al. |
| 6,470,213 B1 | 10/2002 | Alley |
| 6,481,292 B1 | 11/2002 | Reich |
| 6,503,208 B1 | 1/2003 | Skovlund et al. |
| 6,533,733 B1 | 3/2003 | Ericson et al. |
| 6,537,232 B1 | 3/2003 | Kucharczyk et al. |
| 6,589,189 B2 | 7/2003 | Meyerson et al. |
| 6,626,902 B1 | 9/2003 | Kucharczyk et al. |
| 6,636,769 B2 | 10/2003 | Govari et al. |
| 6,682,490 B2 | 1/2004 | Roy et al. |
| 6,724,310 B1 | 4/2004 | Gershenfeld et al. |
| 6,731,976 B2 | 5/2004 | Penn et al. |
| 6,770,030 B1 | 8/2004 | Schaupp et al. |
| 6,796,942 B1 | 9/2004 | Kreiner et al. |
| 6,855,115 B2 | 2/2005 | Fonseca et al. |
| 6,891,474 B1 | 5/2005 | Fletcher |
| 7,147,604 B1 | 12/2006 | Allen et al. |
| 7,435,229 B2 | 10/2008 | Wolf |
| 7,485,105 B2 | 2/2009 | Wolf |
| 7,842,004 B2 | 11/2010 | Kassem |
| 2002/0035331 A1 | 3/2002 | Brockway et al. |
| 2002/0038072 A1 | 3/2002 | Muller et al. |
| 2002/0052563 A1 | 5/2002 | Penn et al. |
| 2002/0077553 A1 | 6/2002 | Govari et al. |
| 2002/0087059 A1 | 7/2002 | O'keefe |
| 2002/0099428 A1 | 7/2002 | Kaufman |
| 2002/0151770 A1 | 10/2002 | Noll et al. |
| 2003/0023134 A1 | 1/2003 | Tracey |
| 2003/0032915 A1 | 2/2003 | Saul |
| 2003/0135110 A1 | 7/2003 | Leussler |
| 2003/0216666 A1 | 11/2003 | Ericson et al. |
| 2004/0073137 A1 | 4/2004 | Lloyd et al. |
| 2004/0134991 A1 | 7/2004 | Fletcher et al. |
| 2004/0147871 A1 | 7/2004 | Burnett |
| 2004/0193021 A1 | 9/2004 | Zdeblick et al. |
| 2004/0260229 A1 | 12/2004 | Meir |
| 2005/0027330 A1 | 2/2005 | Govari |
| 2005/0043669 A1 | 2/2005 | Rosenberg |
| 2005/0043670 A1 | 2/2005 | Rosenberg |
| 2005/0165317 A1 | 7/2005 | Turner et al. |
| 2005/0187487 A1 | 8/2005 | Azizkhan et al. |
| 2005/0187488 A1 | 8/2005 | Wolf |
| 2005/0187509 A1 | 8/2005 | Wolf |
| 2005/0197585 A1 | 9/2005 | Brockway et al. |
| 2005/0204811 A1 | 9/2005 | Neff |
| 2005/0277839 A1 | 12/2005 | Alderman et al. |
| 2006/0009699 A1 | 1/2006 | Roteliuk et al. |
| 2006/0020239 A1 | 1/2006 | Geiger et al. |
| 2006/0036208 A1 | 2/2006 | Burnett |
| 2006/0149161 A1 | 7/2006 | Wilson et al. |
| 2006/0189888 A1 | 8/2006 | Hassler et al. |
| 2006/0195043 A1 | 8/2006 | Rutherford et al. |
| 2006/0211944 A1 | 9/2006 | Mauge et al. |
| 2006/0211945 A1 | 9/2006 | Mauge et al. |
| 2006/0211946 A1 | 9/2006 | Mauge et al. |
| 2006/0235310 A1 | 10/2006 | O'Brien et al. |
| 2006/0283007 A1 | 12/2006 | Cros et al. |
| 2007/0049845 A1 | 3/2007 | Fleischman et al. |
| 2007/0118038 A1 | 5/2007 | Bodecker et al. |
| 2007/0167867 A1 | 7/2007 | Wolf |
| 2007/0208293 A1 | 9/2007 | Mansour et al. |
| 2007/0210923 A1 | 9/2007 | Butler et al. |
| 2007/0282210 A1 | 12/2007 | Stern |
| 2008/0058652 A1 | 3/2008 | Payne |
| 2008/0139959 A1 | 6/2008 | Miethke et al. |

(56) References Cited

U.S. PATENT DOCUMENTS

| | | |
|---|---|---|
| 2008/0208083 A1 | 8/2008 | Lin et al. |
| 2009/0107233 A1 | 4/2009 | Kassem |
| 2009/0112103 A1 | 4/2009 | Kassem |
| 2009/0112147 A1 | 4/2009 | Kassem |
| 2009/0112308 A1 | 4/2009 | Kassem |
| 2010/0168673 A1 | 7/2010 | Stergiopulos et al. |
| 2011/0040233 A1 | 2/2011 | Kassem |

FOREIGN PATENT DOCUMENTS

| | | |
|---|---|---|
| DE | 4042335 A1 | 8/1991 |
| DE | 4042336 A1 | 8/1991 |
| EP | 0115548 | 8/1984 |
| EP | 0619101 A1 | 10/1994 |
| EP | 1312302 | 5/2003 |
| EP | 1389477 | 2/2004 |
| EP | 1491137 | 12/2004 |
| EP | 1738792 A1 | 1/2007 |
| JP | 02-003821 A | 1/1990 |
| WO | 91/05575 A1 | 5/1991 |
| WO | 99/53990 A1 | 10/1999 |
| WO | 01/21066 A1 | 3/2001 |
| WO | 2005/046467 A1 | 5/2005 |
| WO | 2006/048664 A2 | 5/2006 |
| WO | 2006117123 | 11/2006 |
| WO | 2007/041843 A1 | 4/2007 |
| WO | 2007081741 A2 | 7/2007 |

OTHER PUBLICATIONS

[No Author Listed] User's Manual HD2114.0-HD2134.0, HD2164.0-HD2114B.0, HD2114, 2-HD2134.2, HD2164.2-HD2114B.2; Rev. 1.0, Delta OHM, Via g. Marconi, 5-35020 Caselle Di Selvazzano (PD)—Italy, pp. 2-6 (2004).

[No Author Listed] Telemetric Integrated Pressure Sensors, product data sheet of Institut Mikroelektronische Schaultungen und Systeme, p. 1, Sep. 2002.

Dobkin et al., "A Radio-Oriented Introduction to RFID-Protocols, Tags and Applications," High Frequency Electronics, 32-46 (2005).

Ekstedt, J., "CSFS Hydrodynamic Studies in Man, 1. Method of Constant Pressure CSF Infusion," J. Neurology, Neurosurgery & Psych.40:105-19 (1977).

European Search Report, Appl. No. 052580800.0, dated May 15, 2006.

European Search Report, EP Application No. 08253545.1-1526, Mailed Mar. 5, 2009.

European Search Report, EP Application No. 08253554, Mailed Feb. 19, 2009.

Ko Wh et al: "Cerebrospinal Fluid Control System," Proceeding of the IEEE, IEEE. New York, US, vol. 76, No. 9, Sep. 1, 1988, pp. 1226-1235, XP000094517 ISSN: 0018-9219.

Kroin, JS, et al., "Long-term testing of an intracranial pressure monitoring device", J. Neurosurg, V. 93, pp. 852-858, 2000.

Sensor Transponder for Pressure and Temperature, data sheet of Institut Mikroelektronische Schaultungen and Systeme, pp. 1-2, Feb. 2000.

Shapiro, K. et al. "Characterization of Clinical CSF Dynamics and Neural Zxis Compliance Using the Pressure-Volume Index: 1. The Normal Pressure-Volume Index," Annals of Neurology, 7(6):508-14 (1980).

U.S. Office Action for U.S. Appl. No. 11/931,151 dated May 15, 2013, 21 pages.

U.S. Office Action for U.S. Appl. No. 11/931,041 (Publication No. US-2009-0107233-A1) dated Dec. 30, 2009, 19 pages.

U.S. Office Action for U.S. Appl. No. 11/931,127 dated May 10, 2012 (26 Pages).

U.S. Office Action for U.S. Appl. No. 11/931,151 dated Feb. 6, 2012.

U.S. Office Action for U.S. Appl. No. 11/931,151 dated Jul. 13, 2012 (23 pages).

U.S. Office Action for U.S. Appl. No. 11/931,151 dated Jul. 19, 2011, 23 pages.

U.S. Office Action for U.S. Appl. No. 11/931,151 dated Feb. 20, 2013, 25 pages.

U.S. Office Action for U.S. Appl. No. 11/931,187 dated Apr. 24, 2012 (10 Pages).

U.S. Office Action for U.S. Appl. No. 11/931,187 dated May 11, 2010, 8 pages.

U.S. Office Action for U.S. Appl. No. 11/931,187 dated May 9, 2011, 7 pages.

U.S. Office Action for U.S. Appl. No. 11/931,187 dated Oct. 31, 2011.

U.S. Office Action for U.S. Appl. No. 11/931,187 dated Oct. 6, 2010, 8 pages.

U.S. Office Action for U.S. Appl. No. 12/913,054 dated Nov. 26, 2012 (11 Pages).

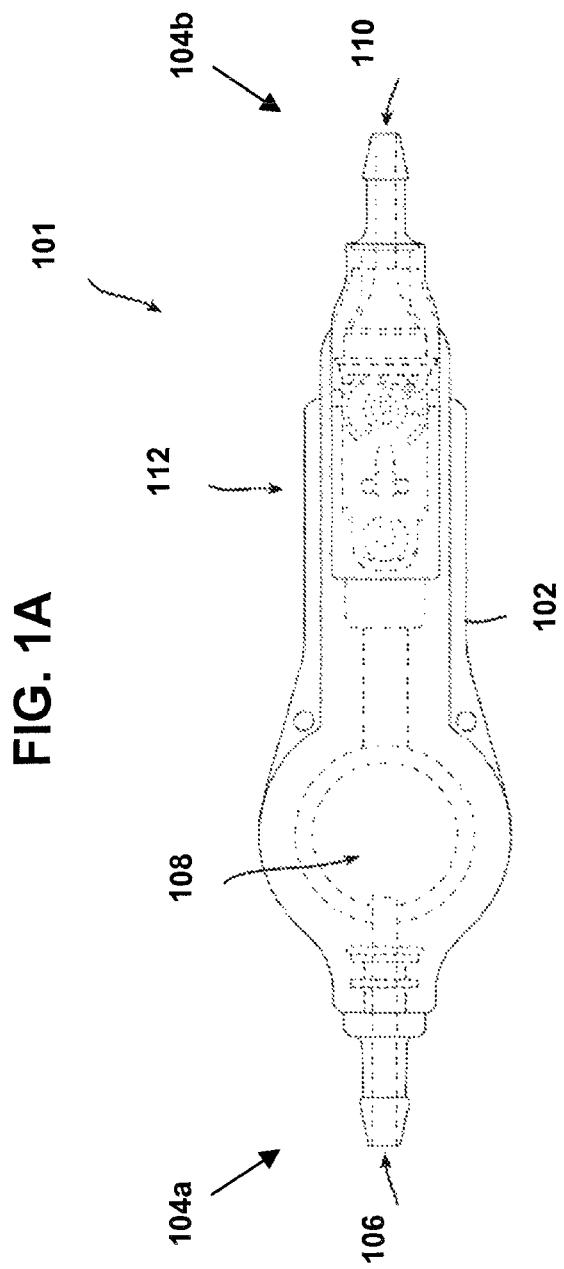

1000

WIRELESS FLOW SENSOR METHODS

CROSS REFERENCE TO RELATED APPLICATION

This application is a divisional of U.S. application Ser. No. 11/931,127, filed on Oct. 31, 2007, and entitled "Wireless Flow Sensor", which is incorporated herein by reference in its entirety.

FIELD

The present application generally relates to devices and methods for non-invasively monitoring and/or measuring the flow of a fluid, and more particularly for monitoring and/or measuring the flow of a fluid in an implantable medical device.

BACKGROUND

It is often desirable to non-invasively monitor or measure the flow of a fluid, for example in an implanted medical device or in a body, and to be able to communicate or indicate the monitoring or measurement information remotely.

By way of illustration, treatment of hydrocephalus can involve monitoring the flow rate of cerebrospinal fluid through a hydrocephalus shunt. Hydrocephalus is a neurological condition that is caused by the abnormal accumulation of cerebrospinal fluid (CSF) within the ventricles, or cavities, of the brain. CSF is a clear, colorless fluid that is primarily produced by the choroid plexus and surrounds the brain and spinal cord, aiding in their protection. Hydrocephalus can arise when the normal drainage of CSF in the brain is blocked in some way, which creates an imbalance between the amount of CSF produced by the choroid plexus and the rate at which CSF is absorbed into the bloodstream, thereby increasing pressure on the brain.

Hydrocephalus is most often treated by surgically implanting a shunt system in a patient. The shunt system diverts the flow of CSF from the ventricle to another area of the body where the CSF can be absorbed as part of the circulatory system. Shunt systems come in a variety of models and typically share similar functional components. These components include a ventricular catheter, which is introduced through a burr hole in the skull and implanted in the patient's ventricle, a drainage catheter that carries the CSF to its ultimate drainage site, and optionally a flow-control mechanism, e.g., shunt valve, that regulates the one-way flow of CSF from the ventricle to the drainage site to maintain normal pressure within the ventricles. It is this flow of CSF which may need to be measured.

In some cases, measuring the flow of CSF can be accomplished by a flow sensor using temperature differentials between two points, e.g., with a mechanism for heating or cooling the CSF in a particular section of the catheter. However, it would be advantageous to provide a flow sensor capable of more accurate and/or direct measurements of flow, without the need for heating or cooling equipment, and to provide a straightforward way to retrieve the measurements from the sensor. Such considerations can apply to a wide range of applications involving the measurement of gas and fluid flow, including CSF, within an implanted device or an embedded, encapsulated, or relatively inaccessible space.

Accordingly, there remains a need for non-invasive monitoring and/or measuring the flow of a fluid, and more particularly for monitoring and/or measuring the flow of a fluid in an implantable medical device.

SUMMARY

In one embodiment, an exemplary implantable sensor for measuring fluid flow is provided. The implantable sensor can have a sensor housing adapted to receive fluid flow therethrough. In some embodiments, the sensor housing can have a domed portion defining a reservoir therein, and the implantable sensor can measure the flow rate of fluid through the reservoir. A radio frequency tag can be located within the sensor housing. The radio frequency tag can be adapted to interact with a wireless signal and to produce a response to the wireless signal. The implantable sensor can also include a masking element that is disposed in the sensor housing. The masking element and the radio frequency tag can be configured to move relative to one another, for example the masking element moving, the radio frequency tag moving, or both, to alter the response of the radio frequency tag and thereby indicate a rate of fluid flowing through the sensor housing. The masking element, for example, can include a conductive member that alters the response of the radio frequency tag by covering at least a portion of it. The response of the radio frequency tag can have at least one characteristic, such as a resonant frequency, harmonic spectra, decay characteristic, and Q factor, that corresponds to the flow rate. In some embodiments, the implantable sensor can also have a valve assembly that is in fluid communication with the sensor housing and that is adapted to control a rate of fluid flowing through the sensor housing.

A wide array of variations are possible. The radio frequency tag can include a disk having an asymmetrical antenna, and the masking element can be configured to mask at least part of the antenna. In some embodiments, the radio frequency tag can also include a chip for storing data and an antenna adapted to communicate the stored data to an external reading device.

Various techniques can be used to associated the radio frequency tag with the flow rate. For example, the masking element can be configured to rotate in response to the flow rate of fluid through the sensor housing. For example, the masking element can include a disk formed at least in part of a conductive material and configured to rotate around an axis thereof. The masking element can be configured to rotate around an axis thereof to mask different parts of the radio frequency tag such that the response of the radio frequency tag to the wireless signal is periodic. The rotation can selectively mask part of the radio frequency tag such that the response of the radio frequency tag to the wireless signal is periodic. The conductive material can be in the form of, for example, a spiral or a plurality of discrete conductive sections. In other embodiments, the masking element can include a disk having a pattern of conductive material formed thereon and a biasing element, such as a spring, calibrated to resist rotation of the disk caused by the flow rate of fluid through the sensor housing. Alternatively, the masking element can have a wedge formed at least in part of a conductive material and the masking element can be configured to translate in relation to the flow rate of fluid through the sensor housing.

In another embodiment, an implantable sensor is provided which has a sensor housing adapted to receive fluid flow therethrough, and a conductive member disposed within the valve assembly. The conductive member can be configured to selectively cover at least a portion of a radio frequency tag and thereby alter a response thereof to a wireless signal to indicate a rate of fluid flowing through the sensor housing. The response of the radio frequency tag can have at least one measurable characteristic, such as resonant frequency, harmonic spectra, decay characteristic, and Q factor, that can indicate the flow rate. In some embodiments, the frequency tag can be configured to move relative to the conductive member, which can result in the frequency tag being selectively covered. The radio frequency tag can also include a disk having an asymmetrical antenna formed thereon. In other embodiments, the conductive member can be configured to move relative to the radio frequency tag, which can result in the frequency tag being selectively covered. The conductive member can form part of a rotatable disk, for example. In some embodiments, the implantable sensor can include a valve assembly that is in fluid communication with the sensor housing and that is adapted to control the rate of fluid flowing through the sensor housing.

In other aspects, an exemplary method for measuring fluid flow is provided and can include positioning a sensor housing between an inlet tube and an outlet tube, the sensor housing having a radio frequency tag disposed therein. The method can further include transmitting a wireless signal to the radio frequency tag from a reading device, and wirelessly receiving a response from the radio frequency tag that indicates a rate of fluid flowing through the sensor housing. In some embodiments, the response can change in relation to the rate of fluid flowing through the sensor housing, and/or it can include a periodic signal. The method can also include analyzing the response to detect any of resonant frequency, harmonic spectra, decay characteristic, and Q factor of an antenna included in the radio frequency tag, and/or receiving a response from the radio frequency tag that communicates data previously stored therein.

In other embodiments, the method can further include coupling the inlet tube to a catheter within a patient's ventricle, and coupling the outlet tube to a drainage catheter for draining the patient's cerebrospinal fluid. The method can also include coupling the sensor housing to a valve assembly adapted to control a rate of fluid flowing through the sensor housing.

BRIEF DESCRIPTION OF THE DRAWINGS

Various exemplary embodiments disclosed herein will be more fully understood from the following detailed description taken in conjunction with the accompanying drawings, in which:

FIG. 1A is a top view of one exemplary implantable valve suitable for use in a hydrocephalus shunt and including a flow sensor.

DETAILED DESCRIPTION

Figure 1B:
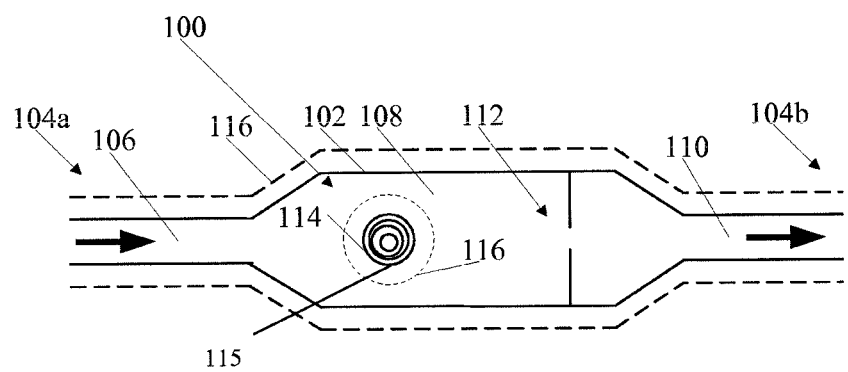
FIG. 1B is a schematic view of one exemplary embodiment of an implantable sensor having a housing with a radio frequency tag and a masking element disposed therein for measuring the flow of a fluid therethrough.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope is defined solely by the claims. The features illustrated or described in connection with one exemplary embodiment may be combined with the features of other embodiments. Such modifications and variations are intended to be included within the scope of the present application.

The present application generally provides methods and devices for non-invasively measuring or quantifying the flow of a fluid through as device and for indicating that information to another device, e.g., telemetrically. The methods and devices are particularly useful in the context of implantable devices, such as hydrocephalus shunts and associated valves. While the description herein sometimes refers to hydrocephalus shunts, one skilled in the art will understand that the devices and methods described herein can be used in a wide variety of methods and devices in which it is desirable to measure fluid flow.

FIG. 1A illustrates one exemplary embodiment of an implantable sensor in the context of an implantable valve for a hydrocephalus shunt. As shown, the implantable valve 101 can include a housing 102 with proximal and distal ends 104a, 104b for receiving fluid flow (such as CSF) therethrough between an inlet port 106 and an outlet port 110. The housing 102 can have virtually any configuration, shape, and size. In many embodiments, the size and shape of the housing 102 can be adapted for implantation in a body, e.g., subcutaneous implantation. In the embodiment shown in FIG. 1A, the housing 102 has a substantially linear configuration with a reservoir 108 having a larger area than the ports 106, 110 which can be advantageous for checking the shunt's patency, tapping the CSF, or to administer therapy. The reservoir 108 can also house a flow sensor, as will be described in more detailed below, and can also house a pressure sensor for measuring the pressure of fluid in the reservoir. For example, suitable pressure sensors are described in co-pending, commonly assigned U.S. patent application Ser. No. 10/907,665, entitled "Pressure Sensing Valve" by Mauge et al., filed Apr. 11, 2005 (now published as U.S. Publication No. 2006-0211946 A1), filed herewith, and in U.S. Pat. Nos. 5,321,989, 5,431,057, and EP Patent No. 1 312 302, the teachings of all of which are hereby incorporated by reference in their entireties. The implantable valve 101 can also include a valve assembly 112 for controlling the flow of fluid through the valve 101 according to remotely or telemetrically selectable settings. A coating can be disposed over the valve 101. Further information on implantable valves can be obtained from U.S. Publication No. 2006-0211946 A1, referenced above.

FIG. 1B schematically illustrates one exemplary embodiment of an implantable sensor in the housing 102. Fluid (e.g., CSF) can flow as indicated by directional arrows through the housing 102 from an inlet (fluid entry) port 106 at the proximal end 104a, through a reservoir 108, and out an outlet (fluid exit) port 110 at the distal end 104b. The reservoir 108 is not necessary (for example, the housing can be in the form of a catheter or tube), but can be advantageous for accommodating other components of the sensor or device therein. The sensor 100 can also have a radio frequency (RF) tag 114 disposed in the reservoir 108, a masking element 115 associated with the RF tag 114 (for clarity, the RF tag 114 and the masking element 115 are represented together in FIG. 1B, although they need not be one component, or be similarly sized and oriented). Moreover, while the RF tag and masking element are shown disposed within the reservoir 108, they can be positioned at any location within a fluid system as long as they can be used to indicate a flow rate of fluid in the system. As will described in more detail below, the RF tag 114 and the masking element 115 can be configured to move relative to one another in response to and/or in relation to the rate of flow of fluid through the housing, and to indicate the rate of fluid flow to an external reading device. In some embodiments, the RF tag 114 can further store data, such as identification information (for example, for the sensor and/or for the patient) and flow rate history, which can be communicated to the external reading device. While not shown, the housing 102 can also contain a valve assembly for controlling the flow of fluid from the inlet port 106 to the outlet port 110, the sensor 100 measuring the controlled flow of fluid therethrough. The proximal and distal ends 104a, 104b of the sensor 100 can each be open and adapted to couple to another medical device, such as a catheter.

Figure 2A:
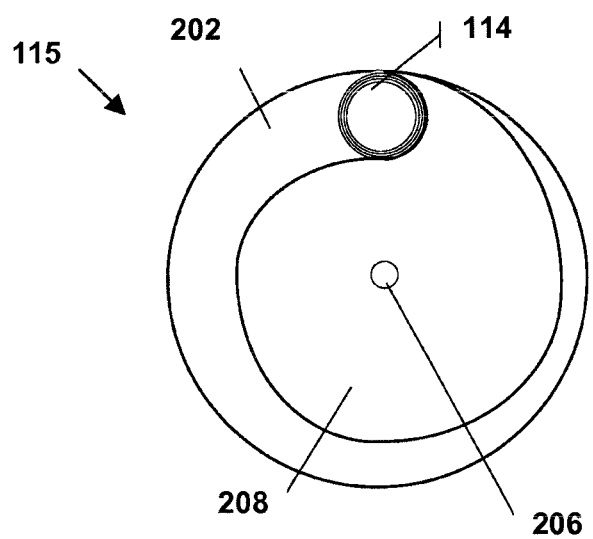
FIG. 2A is a top view of one exemplary embodiment of a radio frequency tag and a masking element for use with the implantable sensor shown in FIG. 1B.
Figure 2B:
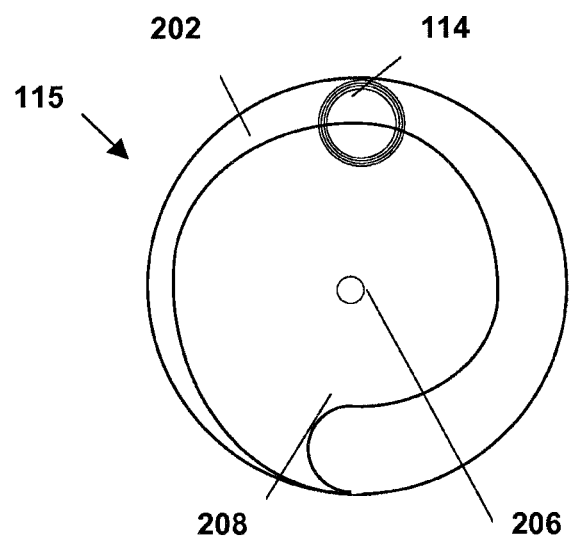
FIG. 2B is a top view of the radio frequency tag and masking element shown in FIG. 2A following rotation of the masking element.

The masking element can have a wide variety of configurations and it can be adapted to interact with the RF tag in a variety of ways. FIG. 2A shows one exemplary embodiment of a masking element 115 associated with an RF tag 114 in which the masking element 115 is in the form of a disk with a conductive portion 202 and a non-conductive (or differently conductive) portion 208. The conductive portion 202 can be a material, such as silver, gold, copper, aluminum, or others known in the art, etc., deposited on the disk. The conductive potion 202 can also be attached or coupled to the disk, or it can be a non-circular portion that fits together with a non-conductive portion 208 to form the complete disk, and so on. The conductive portion 202 can have a variety of shapes, but as shown it is in the shape of a spiral. Alternatively, the conductive portion can be in the shape of a strip of varying width, can have one or more discrete portions of varying size (e.g., a plurality of discrete rectangular shapes), and can have virtually any size and shape that is rotationally asymmetric. As shown in FIG. 2A, the RF tag 114 can be disposed behind the masking element, and particularly behind the spiral portion formed of conductive material 202. (In other embodiments, the RF tag can be disposed behind or in front of the masking element.) In use, the flow of a fluid through a housing 102, such as is shown in FIG. 1, can cause rotation of the masking element 115 about the central axis 206, while the RF tag 114 can remain fixed (for example, fixed relative to the housing shown in FIGS. 1A-1B). FIG. 2B illustrates one possible result of such relative movement. As shown in FIG. 2B, following rotation of the masking element 115, a narrow portion of the conductive material 202 covers the RF tag 114. Accordingly, the response of the RF tag 114 to an external signal (e.g., from a reading device emitting a signal at one or more radio frequencies) in FIG. 2A can differ from that of FIG. 2B and can indicate such relative position and/or movement. For example, in some embodiments, a characteristic of the response of the RF tag 114, such as resonance frequency, harmonic spectra, decay characteristics, or Q factor, can change depending on the relative position or motion of the masking element 115 and the RF tag 114, to indicate the flow rate of fluid within the sensor housing.

Figure 3:
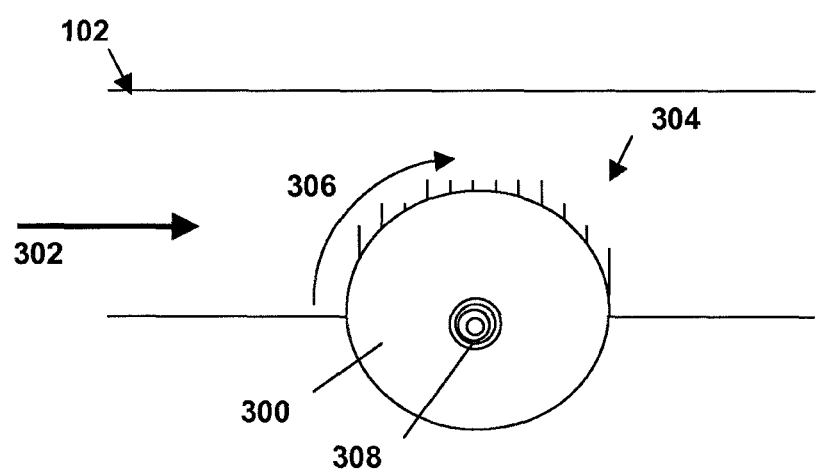
FIG. 3 is a schematic view of an exemplary configuration for coupling the flow of a fluid to a radio frequency tag and/or masking element to cause rotation thereof.
Figure 4:
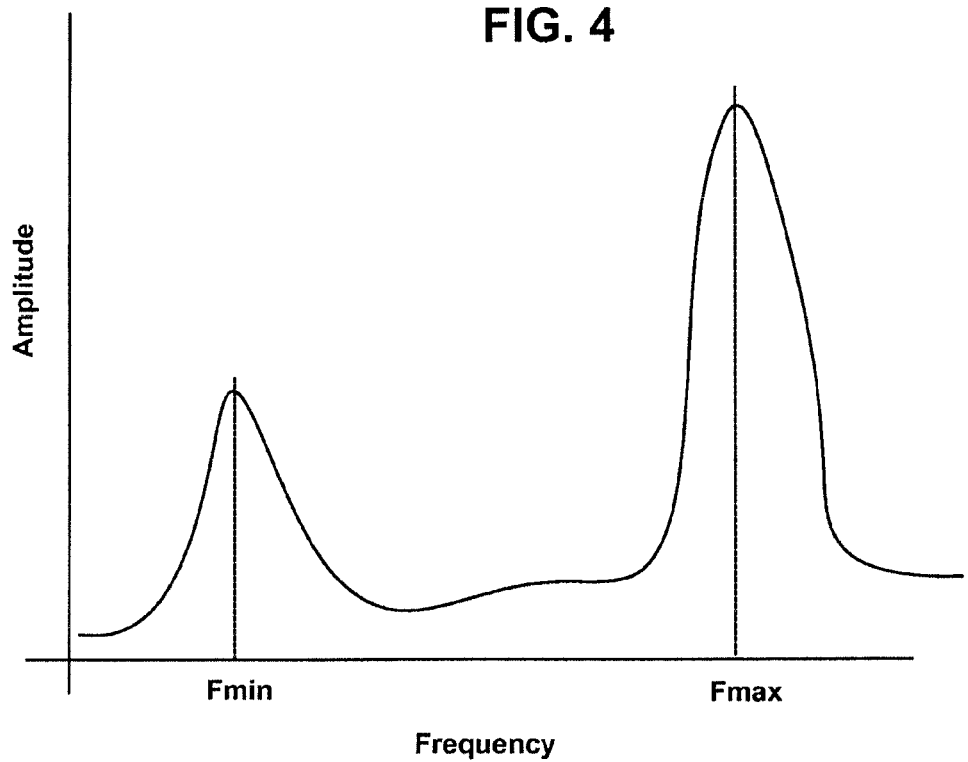
FIG. 4 is a graph illustrating amplitude vs. frequency characteristics of an exemplary response from a radio frequency tag in an implantable sensor.

In some embodiments, the masking element 115 can rotate around its central axis 206 at a speed relative to the RF tag 114 to indicate a fluid flow rate. For example, as shown in FIG. 3, an element 300 can be coupled to fluid flowing in direction 302 in a housing 102 via surface features 304 formed on the element 300, causing the element 300 to rotate as shown by arrow 306. The element 300 can be a masking element 115 itself or alternatively it can be coupled to the masking element 115, for example, via a shaft, gears, and so on. The resulting relative motion of the masking element 115 and the RF tag 114 can be manifested as a periodic radio frequency signal, such as is shown in FIG. 4. The period of the signal (for example, the periodicity of the $f_{max}$ peaks in FIG. 4, or other metric) can be correlated to the flow rate of the fluid.

It should be understood that in some embodiments the nature of the rotation of the masking element 115 relative to the RF tag 114 can vary and can be used to sense or measure other characteristics. In some embodiments, in response to a pressure from flowing fluid the masking element 115 can rotate to a position relative to the RF tag 114 and stop. For example, as shown in FIG. 3, a spring 308 can be disposed on the rotational axis of element 300 to resist the rotation thereof, and the spring 308 can be calibrated such that a given force or pressure causes a known degree of rotation, or rotational deflection, in the element 300. The resulting relative position of the masking element 115 and the RF tag can indicate the pressure via the response of the RF tag to a radio frequency signal, as described above.

Figure 5:
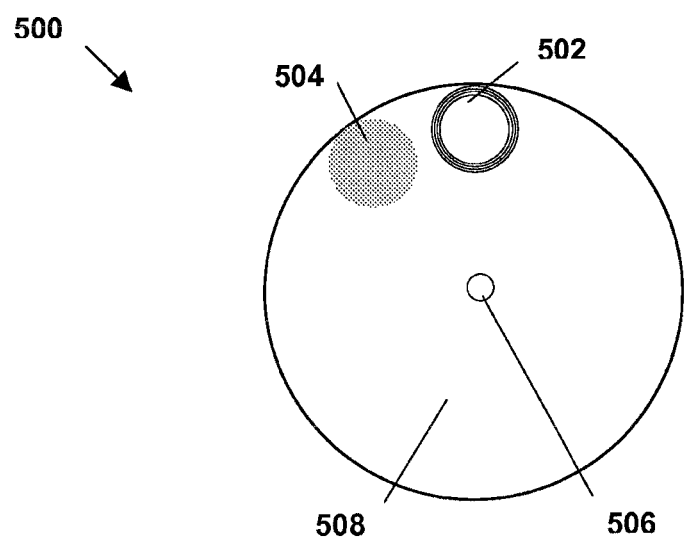
FIG. 5 is a top view of another embodiment of a radio frequency tag and a masking element.

The masking element 115 and the RF tag 114 shown in FIG. 1B can have a wide variety of other configurations. For example, FIG. 5 shows an exemplary masking element 500 in the form of a disk which includes a conductive portion 504 disposed within a disk of non-conductive, or differently conductive, material 508. As shown, the conductive portion 504 is in the form of a circle sized to cover the RF tag 502 completely, although in other embodiments, the conductive portion can be adapted to cover the RF tag 502 partially. The masking element 500 can be coupled to flowing fluid so as to rotate around a central axis 506 in relation to the rate of flow, as previously described. Rotation of the masking element 500 can result in a periodic sudden change or discontinuity in the RF tag's response and thereby indicate the flow rate.

Figure 6:
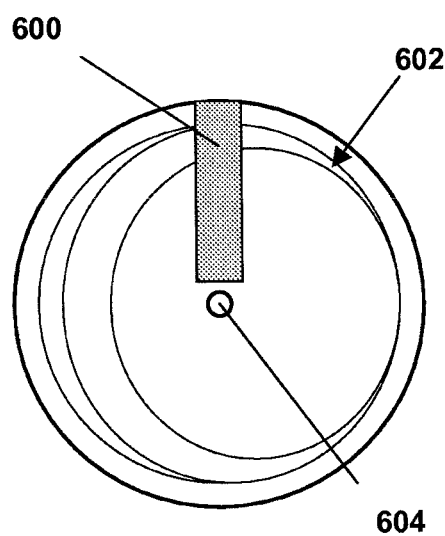
FIG. 6 is a top view of another embodiment of a radio frequency tag and a masking element.

In another embodiment, shown in FIG. 6, a masking element 600 can be in the form of a rectangle, square, or virtually any other shape, and it can be associated with an RF tag 602 having an asymmetric shape. For example, the RF tag 602 can be in the form of a disk with a rotationally asymmetric antenna pattern formed thereon. The pattern can include, for example, antenna lines with varying width, spacing, orientation, and so on. The masking element 600 can be fixed within the housing, and the disk forming the RF tag 602 can be coupled to flowing fluid, e.g., in the housing as shown in FIG. 1B, so as to rotate around axis 604 in relation to the flow rate, as previously described. Such rotation can cause a change or variations in the response of the RF tag 602 as the conductive masking element 600 covers different portions of the asymmetric antenna of the RF tag 602. As previously mentioned, the response can have characteristics, such as resonance frequency, harmonic spectra, decay characteristics, and/or Q factor, which can change as a result of such rotation and which can be detected in the response of the RF tag 602 to a radio frequency signal emitted by a reading device. In an alternative embodiment, the RF tag 602 can be fixed within the housing and the masking element 600 can be adapted to rotate around an axis or otherwise move relative to the RF tag 602.

Figure 7A:
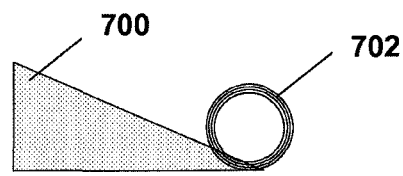
FIG. 7A is a top view of another embodiment of a radio frequency tag and a masking element.
Figure 7B:
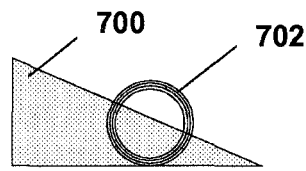
FIG. 7B is a top view the radio frequency tag and masking element shown in FIG. 7A following translation of the masking element and/or radio frequency tag.

In yet another embodiment, the masking element can be configured to translate relative to the RF tag. For example, FIG. 7A shows a masking element 700 formed of a conductive material in the shape of a wedge and associated with an RF tag 702. As the masking element 700 translates relative to the RF tag 702, it covers a different portion of the RF tag 702 (for example as shown in FIG. 7B), resulting a measurable difference in the RF tag's response, as previously described. The masking element 700 can be coupled to the flow of fluid through the sensor housing in a variety of configurations. For example, the configuration described above in connection with FIG. 3 can be adapted such that rotation of the element 300 causes translation of the masking element 700, for example via a rack and pinion gearing.

Figure 8:
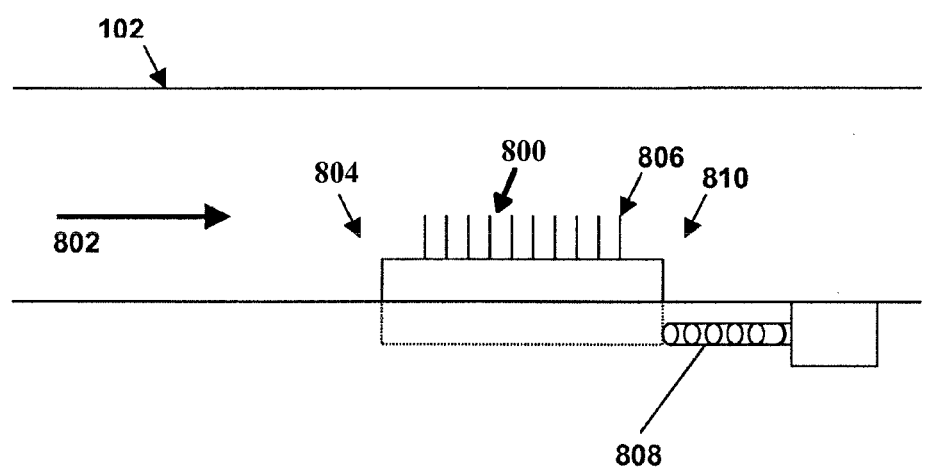
FIG. 8 is a schematic view of an exemplary configuration for coupling the flow of a fluid to a radio frequency tag and/or masking element to cause translation thereof.

Alternatively, as shown in FIG. 8, a sliding element 800 can be disposed in a housing 102. The sliding element 800 can be configured to receive a force of fluid flowing in direction 802 against a proximal end 804 thereof or against elements 806, and to translate in response thereto. A spring 808 or other biasing element can be configured to provide a force against a distal end 810 of the sliding element 800 that resists the force presented on the sliding element 800 by flowing fluid, and the spring 804 can be calibrated such that the deflection of the sliding element 800 corresponds to a force or pressure from the fluid flow. The sliding element 800 can be coupled to a masking element, such as masking element 700, to effect translational movement thereof.

As one skilled in the art will appreciate, the masking element and the RF tag can have a wide variety of further configurations, including virtually any configuration in which a masking element and an RF tag move relative to one another to measure a rate of fluid flow and/or pressure. For example, in some embodiments a variety of masking element shapes can be provided, in some embodiments only one or both of the masking element and the RF tag can be configured to move relative to the other, and so on. In some embodiments, the masking element can physically contact the circuit of the RF tag to thereby change its properties (resistance, capacitance, inductance, etc.) and/or alter connections between conductive elements on the RF tag, for example connecting conductive branches of a circuit, or breaking such connections. In other embodiments, the masking element covers or is disposed in between the reading device and the RF tag. The location of the RF tag and masking element can vary within the housing and are not limited to those shown in the illustrated embodiments. In addition, any mechanism suitable to convert the flow of a fluid to rotational or translational movement can be provided, the foregoing embodiments being by way of example only. Further, many of the embodiments described herein can be adapted to determine or can be correlated to a pressure of fluid in a housing rather than a flow rate.

Returning to FIGS. 1A-1B, the shape, technical specifications, and size of the RF tag 114 can vary widely. In many embodiments, a relatively small RF tag can be used so as to minimize the footprint of the tag in the device, for example with dimensions in a range of about 5 mm to 10 mm, but in other embodiments, tags with dimensions of about 3 mm to 50 mm can be used and any size is possible.

It should be understood that in many embodiments, the RF tag 114 can be chipless, and its physical/electromagnetic parameters can be used to determine a flow rate. The RF tag 114 need not have the capability to store data or to communicate according to a protocol, and need not have processing circuitry or digital logic. A chipless RF tag can provide a circuit (for example, having measurable characteristics, such as a tank circuit) and can be powered from the reading device signal. Such an RF tag can be advantageous due to its relatively low power requirements, and need not have the ability to communicate stored data or "identify" itself. However, in other embodiments the RF tag 114 can be chip-based, and can provide data storage for storing additional information related to the application. An example of chip-based tags are the commonly used RF identification tags. Some of these RF identification tags provide minimal information (such as a TRUE or FALSE value), while others can store several bytes of data. A chip-based RF tag can include processing circuitry, digital logic, a separate antenna, and/or a battery. For example, the RF tag 114 can include a memory for storing data related to the patient and/or sensor. By way of non-limiting example, the RF tag 114 can store sensed pressure data, sensor identification information (e.g., implantation date, sensor type, and sensor identifier code), sensor calibration data, historical data stored from the sensor, tag identification information (e.g., implantation date, tag type, and tag identifier code), and/or patient data (e.g., desired CSF flow rate, previous sensor measurements, and patient medical history). An external reading device, described further below, can read and/or store data in such an RF tag 114.

The RF tag 114 can have any shape, such as elliptical (including circular) or rectangular (including square), and can have virtually any size. The following table lists, by way of example only, available RF tags suitable for use with the devices and methods described herein. Passive as well as semi-passive and active tags can be used, although semi-passive and active tags sometimes are larger than passive tags because they may have an internal battery, e.g., for power purposes.

TABLE 1

| Tag Type | Frequency | | | | | |
|---|---|---|---|---|---|---|
| | 125 KHz | 5-7 MHz | 13.56 MHz | 303/433 MHz | 860-960 MHz | 2.45 GHz |
| Passive | ISO11784/5, 14223 | ISO10536 | (ISO15693) | — | ISO18000-6 | ISO18000-4 |

TABLE 1-continued

| Tag Type | Frequency | | | | | |
|---|---|---|---|---|---|---|
| | 125 KHz | 5-7 MHz | 13.56 MHz | 303/433 MHz | 860-960 MHz | 2.45 GHz |
| | ISO18000-2 | iPico DF/iPX | (ISO15693) MIFARE (ISO14443) Tag-IT (ISO15693) ISO18000-3 | | Electronic Product Code ("EPC") Class 0 EPC Class 1 EPC GEN II Intellitag tolls (Title 21) rail (Association of American Railroads ("AAR") S918) | Intellitag μ-chip |
| Semi-Passive | — | — | — | — | rail (AAR S918) Title 21 | ISO18000-4 Alien BAP |
| Active | — | — | — | Savi (American National Standards Institute ("ANSI") 371.2) ISO18000-7 RFCode | — | ISO18000-4 WhereNet (ANSI 371.1) |

Figure 9A:
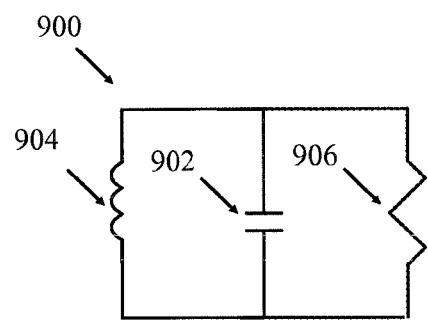
FIG. 9A is a schematic diagram of one exemplary model of a circuit having resonance characteristics.
Figure 9B:
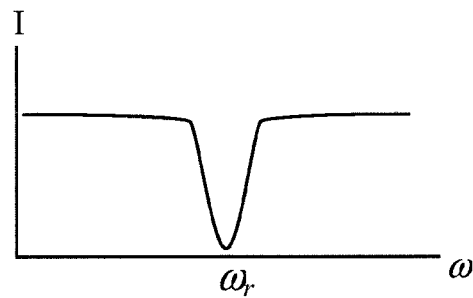
FIG. 9B is a graph of an output voltage signal as a function of frequency for the circuit shown in FIG. 9A.
Figure 9C:
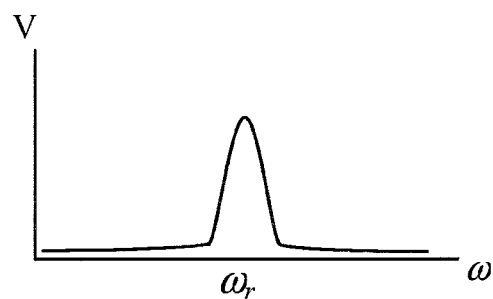
FIG. 9C is a graph of an output voltage signal as a function of frequency for the circuit shown in FIG. 9A.

By way of further explanation, one exemplary circuit for modeling an RF tag can be generally represented by a resonator circuit 900 as shown in FIG. 9A. The circuit 900 includes a capacitor 902, an inductor 904, and an intrinsic resistance 906. When the RF tag is embedded in a sensor and associated with a masking element, as described above, shifts in the resonant frequency of the circuit 900 can be monitored on a continuous or intermittent basis to measure a rate of fluid flow through the housing. The resonant frequency of the circuit 900 can be detected in a variety of ways, such as by measuring power reflected from the circuit 900 or measuring decaying circulating power of the circuit 900 following a outside signal (e.g., from a reading device). FIG. 9B illustrates an example of a graph showing an output signal of the circuit 900 when introduced to an outside signal. The reflected power of the circuit 900 is at a minimum at the resonant frequency, where w can be expressed as:

$$\omega = 2\pi f = \frac{1}{\sqrt{LC}}$$

with f representing the resonant frequency, L representing inductance of the inductor 904, and C representing capacitance of the capacitor 902. FIG. 9C illustrates another example of a graph showing an output signal of the circuit 900 when introduced to an outside signal. The reflected power of the circuit 900 in this example is at a maximum at the resonant frequency. Further examples of such RF tags and information on the use of them, including techniques for interrogating them, can be obtained from U.S. Pat. Nos. 6,025,725, and 6,278,379, and U.S. Patent Application Publication No. 2004/0134991, all of which are hereby by incorporated by reference in their entireties.

Referring again to FIGS. 1A-1B, the housing 102 can be formed from a variety of materials. In one exemplary embodiment, however, the housing 102 is formed from a flexible, biocompatible material. Suitable materials include, for example, polymers such as silicones, polyethylene, and polyurethanes, all of which are known in the art. The housing 102 can also optionally be formed from a radio-opaque material. A person skilled in the art will appreciate that the materials are not limited to those listed herein and that a variety of other biocompatible materials having the appropriate physical properties to enable the desired performance characteristics can be used.

The valve 101, the sensor 100 and/or the RF tag 114 and masking element 115 can also optionally include a coating 116 that is adapted to hermetically seal all or at least a portion of the RF tag 114 and/or masking element 115. The coating 116 can be applied to only a portion of the RF tag 114 and/or masking element 115 that could be exposed to fluid. The RF tag 114 and the sensor 100 can be coated separately, with different coatings, or together in a single coating. An adhesive or other mating technique can optionally be used to affix the RF tag 114 and/or masking element 115 within the reservoir 108, however, in some embodiments it can be useful to allow the RF tag 114 and/or masking element 115 to be removed from the sensor 100 if necessary. Alternatively, the sensor 100 can be coated after the RF tag 114 and/or masking element 115 are disposed in the reservoir 108 to form a protective sheath. The ports 106, 110 can be protected from any coating applied thereto, formed after the coating is applied, or be cleared of any coating applied thereto to allow fluid to flow therethrough. In other embodiments, only certain components of the sensor 100 can be coated. A person skilled in the art will appreciate that a variety of other techniques can be used to seal the components of the sensor 100.

The material used to form the coating 116 can vary, and a variety of techniques can be used to apply the coating. By way of non-limiting example, suitable materials include polyurethane, silicone, solvent-based polymer solutions, and any other polymer that will adhere to the components to which it is applied to, and suitable techniques for applying the coating include spray-coating or dip-coating.

Figure 10:
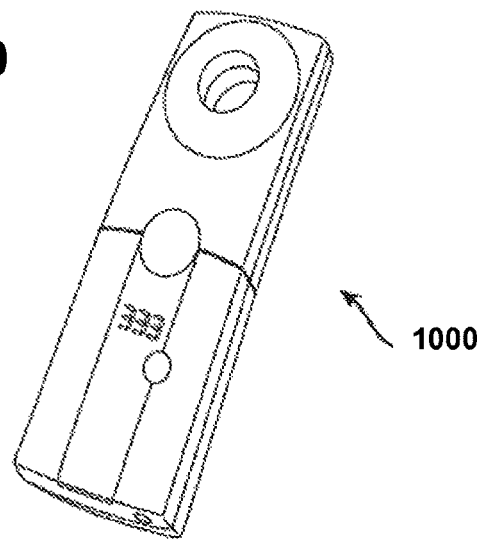
FIG. 10 is a perspective view of an exemplary reading device for reading a flow rate from an implantable sensor; and, FIG. 11 illustrates the implantable sensor shown in FIG. 1 implanted in a body and being read by the reading device shown in FIG. 10.
Figure 11:
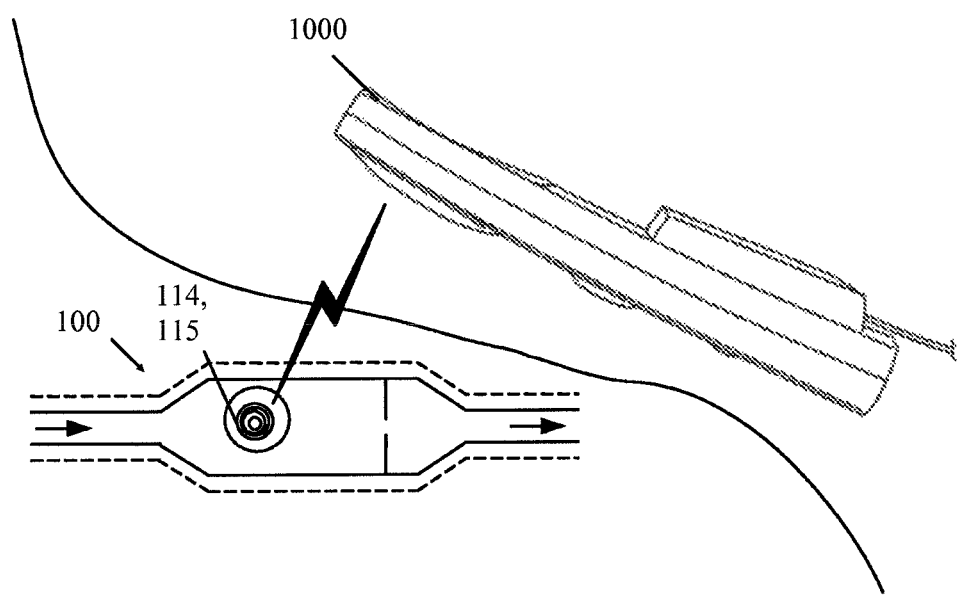

FIG. 10 shows one exemplary embodiment of a reading device 1000, such as an RF telemetry device, for use in obtaining information from the RF tag 114. The reading device 1000 can emit a signal at one frequency or over a range of frequencies, and can listen for the response thereto, e.g., from the RF tag 114. In the case of a chipless RF tag, a characteristic of the response from the tag can indicate a measured flow rate, as explained previously. In the case of a chip-based RF tag having memory associated therewith, the response of the tag can communicate information (e.g., according to a communication protocol) stored in its memory for the reading device. Any type of external reading device can be used. In one exemplary embodiment, the reading device 1000 can include an RF module (e.g., transmitter and receiver), a control unit (e.g., microcontroller), a coupling element to the transponder (e.g., antenna), and an interface (e.g., Recommended Standard (RS) 232, RS-485, Firewire, Universal Serial Bus (USB), Bluetooth, ZigBee, etc.) to enable communication with another device (e.g., a personal computer). The reading device 1000 can provide the power required by the RF tag 114 to operate, e.g., via inductive coupling. As shown in FIG. 11, the reading device 1000 can be positioned in proximity to an implanted RF tag 114 to telemetrically communicate with the RF tag 114, and thereby obtain a reading of the measured flow rate.

In another aspect, a method for measuring a rate of fluid flow is provided. In one embodiment, an exemplary method can include implanting a flow sensor, such as the flow sensor 100 described above in connection with FIGS. 1A and 1B, in a body. In the case of a hydrocephalus shunt, a hydrocephalus valve including the flow sensor can be subcutaneously implanted in a patient, as shown in FIG. 11. It should be understood that while FIG. 12 shows the implantation of a flow sensor in a shoulder region, the device can be implanted virtually anywhere, for example subcutaneously behind the ear, or on the head, torso, etc. The method can also include coupling a proximal end of a catheter, such as a ventricular catheter, to an inlet port of the flow sensor. Another catheter, such as a drainage catheter, can be coupled to an outlet port of the flow sensor. The drainage catheter can extend through the patient to an area where excess fluid, e.g., CSF, can drain safely.

The method can further include wirelessly transmitting a wireless signal to an RF tag embedded in the flow sensor, for example using a reading device such as reading device 1000 described above in connection with FIG. 10. The transmitted signal can be include one or more frequencies. In some embodiments, the wireless signal can be transmitted according to a protocol in order to communicate with an RF tag having a chip therein. The method can also include receiving a response from the RF tag that indicates a rate of fluid flowing through the sensor housing. The response can have one or more characteristics, such as resonance frequency, harmonic spectra, decay characteristics, and Q factor, that can be detected and analyzed in order to determine a measured rate of flow. In some embodiments, the response from the RF tag can be static, not changing over time unless the rate of fluid flow changes. In other embodiments, the response from the RF tag can exhibit periodicity, and analysis of the response can include determining a rate of flow based on the periodicity of the response signal. The determination of a flow rate can be performed using calibration data for a particular flow sensor. In some embodiments, the calibration data, as well as other data such as identification and/or historical data, can be transmitted from an RF tag having a memory to the reading device.

Further information on wireless shunts can be obtained from U.S. Pat. No. 7,842,004 entitled "Wireless Pressure Setting Indicator" by Salim Kassem, U.S. patent application Ser. No. 11/931,151 entitled "Wireless Pressure Sensing Shunts" by Salim Kassem, and U.S. patent application Ser. No. 11/931,187 entitled "Wireless Shunts With Storage" by Salim Kassem, all of which were filed on Oct. 31, 2007 and which are hereby incorporated by reference in their entirety. Also incorporated by reference in its entirety is commonly assigned U.S. Pat. No. 7,510,533, entitled "Pressure Sensing Valve."

A person skilled in the art will appreciate that the various methods and devices disclosed herein can be formed from a variety of materials. Moreover, particular components can be implantable and in such embodiments the components can be formed from various biocompatible materials known in the art. Exemplary biocompatible materials include, by way of non-limiting example, composite plastic materials, biocompatible metals and alloys such as stainless steel, titanium, titanium alloys and cobalt-chromium alloys, glass, and any other material that is biologically compatible and non-toxic to the human body.

One skilled in the art will appreciate further features and advantages based on the above-described embodiments. Accordingly, the disclosure is not to be limited by what has been particularly shown and described, except as indicated by the appended claims. All publications and references cited herein are expressly incorporated herein by reference in their entirety.

What is claimed is:

1. A method for measuring fluid flow, comprising:
   implanting a sensor in a patient, the sensor including a sensor housing positioned between an inlet tube and an outlet tube, the sensor housing having a radio frequency tag and a conductive member disposed therein, the conductive member being configured to cover the radio frequency tag based on a rate of fluid flowing through the sensor housing;
   transmitting a wireless signal to the radio frequency tag disposed within the implanted sensor housing from a reading device; and
   wirelessly receiving a response from the radio frequency tag that indicates the rate of fluid flowing through the sensor housing,
   wherein the radio frequency tag is configured to move in response to the fluid flowing through the sensor housing, the movement allowing the conductive member to cover different portions of the radio frequency tag.

2. A method for measuring fluid flow, comprising:
   implanting a sensor in a patient, the sensor including a sensor housing positioned between an inlet tube and an outlet tube, the sensor housing having a radio frequency tag and a conductive member disposed therein, the conductive member being configured to cover the radio frequency tag based on a rate of fluid flowing through the sensor housing;
   transmitting a wireless signal to the radio frequency tag disposed within the implanted sensor housing from a reading device; and
   wirelessly receiving a response from the radio frequency tag that indicates the rate of fluid flowing through the sensor housing,
   wherein the radio frequency tag has a rotationally asymmetric antenna pattern formed therein, and the conductive member is configured to cover different portions of the pattern based on the rate of fluid flowing through the sensor housing.

3. A method for measuring fluid flow, comprising:
   implanting a sensor in a patient, the sensor including a sensor housing positioned between an inlet tube and an outlet tube, the sensor housing having a radio frequency tag and a conductive member disposed therein, the conductive member being configured to cover the radio frequency tag based on a rate of fluid flowing through the sensor housing;
   transmitting a wireless signal to the radio frequency tag disposed within the implanted sensor housing from a reading device; and wirelessly receiving a response from the radio frequency tag that indicates the rate of fluid flowing through the sensor housing, wherein the conductive member is configured to rotate with circular motion in response to fluid flowing through the sensor housing, thereby moving the conductive member so as to cover different portions of the radio frequency tag.

* * * * *